United States Patent [19]

Borkan

[11] Patent Number: 4,459,989

[45] Date of Patent: Jul. 17, 1984

[54] NON-INVASIVE MULTIPROGRAMMABLE TISSUE STIMULATOR AND METHODS FOR USE

[75] Inventor: William N. Borkan, North Miami, Fla.

[73] Assignee: Neuromed, Inc., Fort Lauderdale, Fla.

[21] Appl. No.: 278,991

[22] Filed: Jun. 30, 1981

[51] Int. Cl.³ .............................................. A61N 1/36
[52] U.S. Cl. .................................................. 128/421
[58] Field of Search ........ 128/419 PG, 419 F, 419 C, 128/419 E, 421, 423

[56] References Cited

U.S. PATENT DOCUMENTS

3,727,616  4/1973  Lenzkes .......................... 128/419 E
4,049,004  9/1977  Walters ......................... 128/419 PG
4,187,854  2/1980  Hepp et al. ................... 128/419 PG
4,203,447  5/1980  Keller, Jr. et al. ........... 128/419 PG
4,241,736 12/1980  Rossing et al. .............. 128/419 PG

Primary Examiner—William E. Kamm
Attorney, Agent, or Firm—Barnes & Thornburg

[57] ABSTRACT

An electronic tissue stimulator system is provided comprising a plurality of electrodes to be implanted adjacent tissue to be stimulated in a patient. A transmitting means transmits stimulation pulses for stimulating the electrodes and programming data defining which of the electrodes are to be stimulated and the electrical polarity of the electrodes relative to one another. A receiving means to be surgically-implanted within the patient which receives the stimulation pulses and the programming data, and delivers the energy in the stimulation pulses to the electrodes as defined by the programming data.

37 Claims, 13 Drawing Figures

NON-INVASIVE MULTIPROGRAMMABLE TISSUE STIMULATOR AND METHODS FOR USE

BACKGROUND OF THE INVENTION

This invention relates to a partially implanted electronic tissue stimulator system for controlling various neurological and muscular disorders.

The concept of using an electronic stimulation system for the purpose of controlling a nerve or muscle response is well known. This type of system typically utilizes a pulse generator which remains outside the patient's body. A transmitting antenna receives RF energy from the pulse generator and transmits this energy through the patient's skin to a subcutaneous receiver. The receiver provides signal processing of the received pulses and transmits the energy derived therefrom to activate a pair of electrodes implanted adjacent nerve or muscle tissue. The receiver may be powered internally by an electrical supply such as a rechargable battery pack or in the preferred method, by the energy in the transmitted pulses. A system like the one described above is seen in U.S. Pat. No. 3,727,616. It is also known in the prior art to provide a plurality of electrode pairs adjacent a nerve center such that the potential differences between the electrodes and the number of electrode pairs which are energized controls the number of nerve fibers that are stimulated. Such a system is described in U.S. Pat. No. 3,449,768.

A problem arises, however, in these prior art systems, when the electrode placement fails to provide the desired physical response. This failure may also be caused by improper polarity of the stimulated electrodes relative to one another. Furthermore, it is often required that the electrodes be implanted surgically adjacent to one or more nerve fibers. This type of procedure involves inherent risks due to the fact that it is often performed in close proximity to the brain or spinal cord. It is therefore desirable to perform the electrode implantation only one time to minimize the surgical risks to the patient as well as the financial burden. Moreover, even when a plurality of electrodes have been utilized, such that repeated surgical procedures are not required, the prior art systems have not provided for dynamic programming of different electrodes after surgery such that the physician can find the appropriate electrodes that produce a desired response.

The prior art systems have also proven to be somewhat ineffective in practice due to their inability to provide more than one type of stimulation signal to the electrodes. Specifically, in the event that the chosen signal does not provide appropriate treatment, another surgical procedure must be performed to implant a unit which can provide a different type of stimulation signal. Further, even patients who respond to one type of signal might respond better if another type were used, however, the prior art systems do not generally allow the physician such flexibility. Therefore, even though a different stimulation signal might be more beneficial to the patient, the physician will not usually perform additional surgery unless there is no positive response.

The problems of the prior art systems have severely hampered the widespread application of tissue stimulation systems to date, even in areas where they show great promise in relieving disorders which have no other viable treatment alternatives.

SUMMARY OF THE INVENTION

It is therefore an object of the present invention to provide a partially implanted tissue stimulator system wherein the subcutaneous receiver can be non-invasively programmed any time after implant to stimulate different electrodes or change stimulation parameters such that a desired response can be attained. Each electrode is capable of assuming a positive, negative or open-circuit status with respect to the other electrodes.

It is another object of the present invention to provide a tissue stimulator system wherein the electrode programming is derived from programming data which is modulated on a carrier wave. The carrier wave is then transmitted in bursts which define the stimulation pulses for the electrodes.

It is a further object of the present invention to provide a system of the type described wherein the receiver includes circuitry for determining whether the programming data is being received properly. The stimulation pulses are applied to the electrodes only after a predetermined number of consecutive, identical programming data sequences have been received.

It is yet another object of this invention to provide a system of the type described wherein the receiver may not require any internal source of electrical power.

It is still another object of this invention to provide a tissue stimulator system wherein the programming data is retained in the receiver between the reception of stimulation pulses unless the receiver is being reprogrammed or the transmitter is turned off.

It is still another object of this invention to provide a tissue stimulator system wherein the relative polarity of the stimulated electrodes can be kept constant or be alternated during application of consecutive stimulation pulses to the electrodes.

These and other objects of the invention are attained by providing a plurality of electrodes to be implanted adjacent tissue to be stimulated in a patient. A transmitting means transmits stimulation pulses for stimulating the electrodes and programming data defining which of the electrodes are to be stimulated and the electrical polarity of the electrodes relative to one another. A receiving means to be surgically implanted within the patient receives the stimulation pulses and the programming data, and delivers the energy of the stimulation pulses to the electrodes as defined in the programming data.

The programming data is transmitted as a modulated signal on a carrier wave, the carrier wave being transmitted in bursts which define the stimulation pulses. The parameters of the bursts can be varied by the transmitting means such that the stimulation pulses have different pulse parameters. The receiving means includes detector means to demodulate the stimulation pulses from the carrier wave and logic converter means for separating the programming data from the stimulation pulses.

The receiving means further includes an error detection means for comparing consecutive sequences of programming data and controlling delivery of the energy in the stimulation pulses to the electrodes as a function of the comparison, this delivery defining a stimulation mode. In the preferred embodiment of the invention, this energy is delivered to the electrodes after a predetermined number of consecutive, identical sequences of the programming data are received by the receiving means. The receiver is in a programming mode prior to receiving the identical sequences. The receiving means further includes a voltage storage means for storing the steady-state energy derived from the stimulation pulses. Also, a loss of voltage comparator means is provided which continuously compares the energy in the voltage storage means with a predetermined voltage to control the error detection means. The loss of voltage comparator means resets the error detection means when the energy in the voltage storage means is less than the predetermined voltage, this reset serving to return the system to a programming mode.

The receiving means further includes a channel enable means controlled by the programming data and the error detection means for preventing energization of the electrodes until:

(a) the error detection means determines that a predetermined number of consecutive, identical sequences of the programming data have been received, (b) one of two redundant receivers in the receiving means has been selected for operation, and (c) no invalid electrode programming combination which would short the receiving means is defined in the programming data.

The receiving means further includes a memory means, which may be volatile or non-volatile, for storing the programming data and a mono/biphasic control means connected to the memory means for controlling the relative polarity of the stimulated electrodes during application of consecutive stimulation pulses. Also, the receiving means includes an output control logic means connected to the memory means, the output control logic means being controlled by the channel enable means. A plurality of output switches are connected to the output control logic means and are controlled by the programming data to deliver the energy in the stimulation pulses to the electrodes.

The receiving means further includes a delay means for controlling the output control logic means to delay the application of the stimulation pulses to the output switches. A clock circuit means is provided for controlling the delay means and for applying the programming data to the memory means. The period of the delay means is at least equal to the period of a programming data sequence such that the stimulation pulses are not applied to the output switches until after the programming data sequence has been stored in the memory means.

The receiving means may be powered by the energy transmitted by the transmitting means, or alternatively, by an internal energy source, or a combination of both sources.

The invention also contemplates a method of providing tissue stimulation comprising the steps of surgically-implanting a receiving means in the patient, surgically-implanting a plurality of electrodes connected to the receiving means adjacent tissue to be stimulated in the patient, selected first programming data defining which of the electrodes will be stimulated and the electrical polarity of the electrodes relative to one another, and transmitting the first selected programming data to the receiving means to produce a response. Should the first programming data fail to produce a desired response, the method further provides for: selecting second programming data, different from the first programming data; defining a new combination of electrodes to be stimulated or a new polarity of the stimulated electrodes; and transmitting this second selected programming data to the receiving means. The method further provides for trial of various electrode combinations and polarities at various stimulation pulse frequencies, widths, and amplitudes such that the appropriate combination of these parameters may be combined to provide a desired response.

BRIEF DESCRIPTION OF THE DRAWINGS

FIG. 3 shows signal waveforms at various stages of the receiver circuitry.

DESCRIPTION OF THE PREFERRED EMBODIMENT

Figures 1, 2, 3A, 3E:
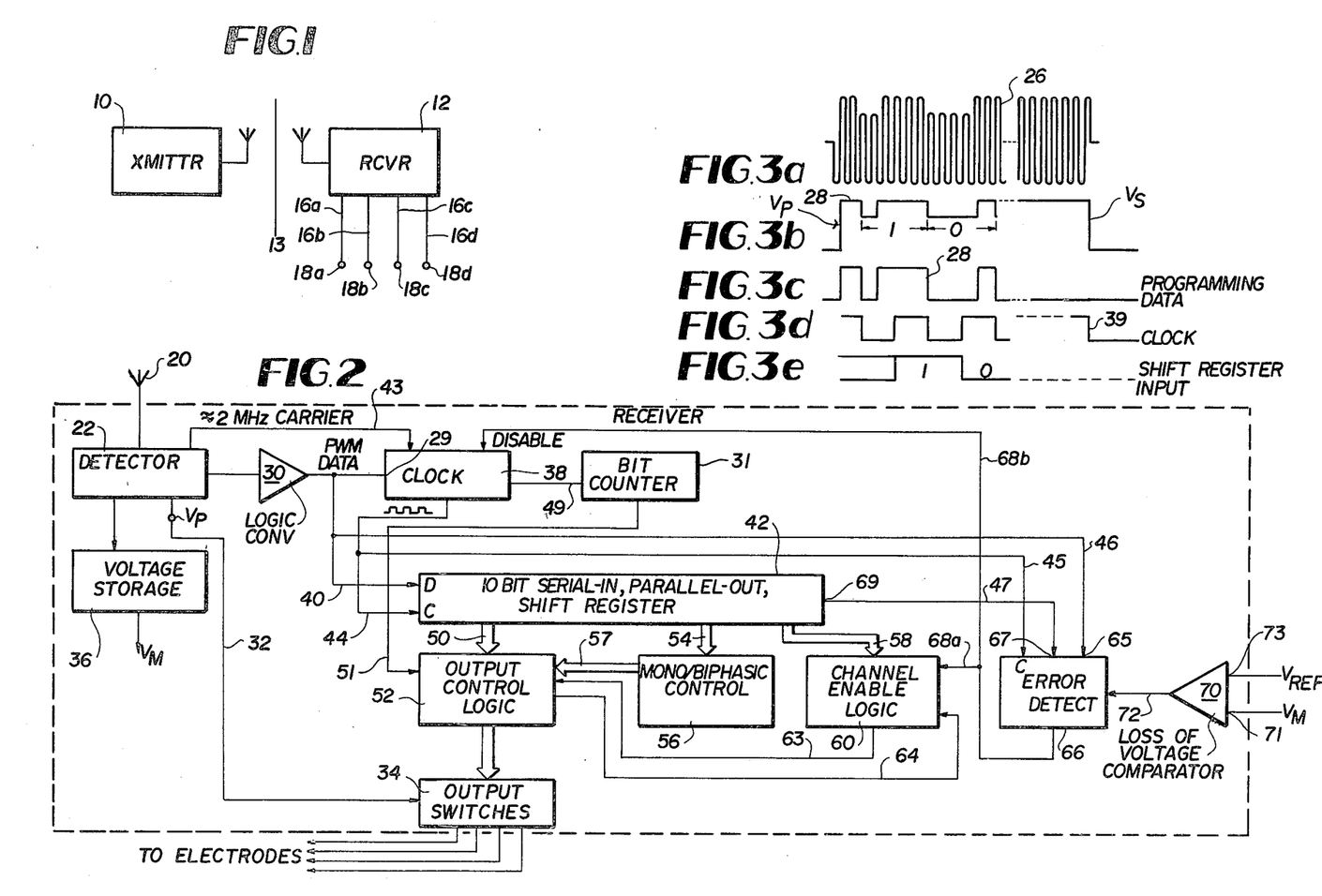
FIG. 1 is a simple block diagram of the overall system of the invention.
FIG. 2 is a block diagram of the receiver of the invention.

Referring now to the drawings, specifically FIG. 1, a simplified block diagram of the overall system is provided. The system includes a transmitter 10 and a receiver 12, the latter being surgically implanted beneath the patient's skin 13. The output of the receiver 12 is coupled via a plurality of lead wires 16a–16d to a plurality of electrodes 18a–18d. In the preferred embodiment of the invention, four leads are utilized, however, any convenient number of electrodes may be implanted as desired. Electrodes 18 are implanted adjacent the tissue to be stimulated, for example, nerve or muscle tissue. The receiver 12 may be manufactured by thick or thin-film hybrid technology or on a single integrated circuit using state-of-the-art techniques.

The transmitter 10 of the present invention includes programming controls (not shown) as well as transmitting circuits. In operation, the attending physician is required to select the specific pulse parameters that he desires for a specific patient. Through the programming controls, programming data is generated as a function of the physician's selection. This data generally includes control information defining which of the electrodes 18 are to be stimulated, as well as the electrical polarity of these electrodes relative to one another. It is an important feature of the present invention that each of the electrodes 18 is capable of assuming a programmed positive, negative or open-circuit status with respect to the other electrodes. Using the programming controls, the physician can modify the electrical configuration of the electrodes 18 to obtain the best response possible for the patient. If the selected electrodes fail to produce the desired response, the physician need only reprogram the transmitter 10 and transmit the new programming data.

The transmitter 10 includes a source of sinusoidal energy which functions as a carrier signal. In the preferred embodiment of the invention, the programming data is a pulse width modulated signal which is amplitude modulated onto the carrier signal by a modulation circuit. Such a circuit is well known in the art and forms no part of the instant invention. It should be recognized that although a pulse-width modulated signal is specifically discussed, any other type of digital, magnetic, or analog signal capable of defining the programming data may be utilized. The carrier is pulsed on and off as a "burst" signal to form the stimulation pulses which are transmitted by the transmitter 10 to the receiver 12. The parameters of the burst, such as amplitude, frequency and width, are preferably selected by the attending physician through the programming controls such that the resulting stimulation pulse signal can have different wave-shapes. Also, the electrode impedance at specific frequencies and locations can be used to help determine which electrodes give the best response. This flexibility allows the physician to further control the stimulation response.

Note that although the transmitter 10 is shown in FIG. 1 as located external to the patient, it should be recognized that this placement is not meant to be limiting. The transmitter may also be implanted in the patient and be reprogrammed by measured internal physiological variables and/or a combination of external programming, measured variables and specific preprogrammed stored parameters. It may also be desirable to have the transmitter and receiver formed as an integral unit using internal and/or external power and programming sources.

Turning now to FIG. 2, a block diagram of the receiver 12 is shown. This device includes an antenna 20 coupled to a detector circuit 22 which provides envelope detection of the transmitted signal to remove the carrier signal. With reference to FIG. 3a, the transmitted burst is shown comprising the carrier signal 26 which includes the pulse width modulated programming data riding as a ripple. The output of the detector circuit 22 is seen in FIG. 3b as an envelope of the transmitted burst with the carrier removed, and includes the transmitted pulse $V_p$ and the programming data 28 modulated thereon. It should be noted that the transmitted pulse $V_p$ includes the stimulation pulse $V_s$ as seen in FIG. 3b. In particular, the stimulation pulse $V_s$ is that portion of the transmitted pulse $V_p$ which doesn't include the programming data sequence. In the preferred embodiment of the invention, the programming data 28 is modulated on the first half of the transmitted pulse $V_p$. Therefore, the second half of the transmitted pulse $V_p$ is used as the stimulation pulse $V_s$.

The output of the detector circuit 22 is connected to a logic converter circuit 30 which decodes the programming data 28 from the transmitted pulse $V_p$. The transmitted pulse $V_p$ which includes the stimulation pulse $V_s$, is routed via conductor 32 to the output switches 34 connected to the electrodes 18. The steady state or long-term energy derived from the received pulses is stored in a voltage storage circuit 36 as a voltage signal $V_m$. The decay time of the voltage signal $V_m$ is much longer as compared with the time between reception of the transmitted bursts, and therefore this voltage is used to power the receiver circuitry between the reception period. This feature also allows for continued system operation during those brief periods when the receiver might lose the transmitted signal due to dislocation of the antenna 20 during routine activities of daily living. It should be noted that a small, internal power source could be incorporated into the receiver to augment or replace the voltage storage circuit 36. Such an internal power source serves to convert the receiver memory, to be described below, into a nonvolatile memory. Thus, once the receiver is programmed, stimulation can be achieved by transmitting stimulation pulses without the programming data. In practice, the physican will program the receiver at the hospital using a sophisticated transmitter. The patient would then require only a simple transmitter at home which could derive stimulation pulses.

The output of the logic converter circuit 30 is seen in FIG. 3c and consists of the pulse-width modulated programming data 28 defining which of the electrodes 18 are to be stimulated, the electrical polarity of these electrodes relative to each other, whether the electrodes will be stimulated in the mono or biphasic mode, and which of two redundant receivers or channels (if two are used) are to be activated. The monophasic mode is one wherein the polarity of the stimulated electrodes is kept constant. In the biphasic mode, the relative polarity of the stimulated electrodes reverses with each stimulation cycle. The programming data 28 is applied to input 29 of a clock circuit 88 which forms clock pulses 39 for the rest of the receiver circuitry. These clock pulses, which are seen in FIG. 3d, have a duty cycle which is a function of the carrier frequency, the carrier signal being applied to the clock circuit via conductor 43. The programming data 28 is further applied via conductor 40 to the data input of a memory comprising a serial-in, parallel-out shift register 42. This data 28 is clocked into the data input of the shift register by the clock pulses 39 produced by the clock circuit 38 and delivered to the clock input of the shift register via conductor 44. The data input to the shift register is seen in FIG. 3e.

The shift register 42 includes a first output data bus 50 for connecting a portion of the programming data 28 to an output control logic circuit 52. This portion of the programming data determines which electrodes will be stimulated and the relative positive or negative polarity of these electrodes. The output control logic circuit 52 drives the plurality of output switches 34 to route the stimulation pulses $V_s$ from conductor 32 to the appropriate electrodes 18 defined in the programming data 28.

The shift register 42 includes a second output data bus 54 which connects a second portion of the programming data 28 to a mono/biphasic control circuit 56. This circuit allows the physician to program for stimulation pulses of alternating polarity. As stated above, in the monophasic mode, the relative polarity of the stimulated electrodes remains constant; however, in the biphasic mode, this polarity reverses on each stimulation cycle. This feature is selected during programming by the programming controls and is transmitted as a portion of the programming data 28. The output of the mono/biphasic control circuit 56 is connected to the output control logic circuit 52 via conductor bus 57 such that the mono or biphasic parameter can be used to control the stimulation pulses applied to the electrodes.

A third output data bus 58 of the shift register 42 connects a final portion of the programming data 28 to a channel enable logic circuit 60. This circuit is incorporated to allow for the possibility of adding a second receiver. In particular, the channel enable programming data, also programmed by the physician, may specify which of two redundant circuits in the same receiver package, A or B, is to be activated by the stimulation pulses. This feature is desirable should one receiver become defective or a second receiver be required to stimulate another group of electrodes in a separate region of the patient's body. More importantly, the output of the channel enable logic circuit 60 also controls the routing of the programming data 28 through the output control logic circuit 52. In particular, when the channel enable logic circuit is activated, as would only occur when (a) the appropriate channel A or B has been selected, (b) a predetermined number of consecutive, identical programming data sequences have been received, and (c) no invalid electrode combinations which would short the receiver have been selected, a pulse on conductor 63 is transmitted to output control logic circuit 52. This signal, in combination with the output of bit control circuit 31, to be described below, is used to control the application of the stimulation pulses $V_s$ to the output switches 34. Note that if an invalid combination is selected, a disable signal is outputed from the output control logic circuit 52 on conductor 64.

The pulse-width modulated programming data 28 is also applied to one input 65 of an error detection circuit 66 via conductor 46. The other input 67 of the error detection circuit is provided by the serial output 69 of the last bit of the shift register 42 over conductor 47. The clock pulses 39 are also applied via conductor 45. When the error detection circuit determines that a predetermined number of consecutive, identical sequences of programming data have been received, an output enable signal is provided via conductor 68a to enable the channel enable logic circuit 60. In the preferred embodiment, four consecutive, identical sequences are required. A bit counter circuit 31 shown in FIG. 2 receives a signal over conductor 49 from clock circuit 38. The bit counter is a $\div 10$ flipflop configuration commonly known in the art. The output of this circuit is used to control the output control logic such that the output switches cannot be turned on until the ten data bits of the programming data sequence have been received. This circuit thus forms delay means for delaying application of $V_p$ to the electrodes. Therefore, only the stimulation pulse $V_s$ of $V_p$ will be applied to the output switches. As described above, the channel enable logic circuit 60 and the bit counter circuit 31 control the output control logic circuit 52 and the output switches 34 to deliver the energy of the stimulation pulses $V_s$ to the electrodes 18 defined in the programming data 28. During stimulation, the output enable signal from the error detection circuit 66 functions to turn the clock circuit 38 off via conductor 68b. The programming data, however, remains in the shift register 42 until the voltage Vm decays to a predetermined value, such as will occur when the transmitter is turned off or the antenna 20 is decoupled from the receiver. Thus, once four consecutive, identical programming data sequences are received and the channel enable logic circuit 60 is enabled, the subsequently-received stimulation pulses are applied to the electrodes without further programming after the bit counter circuit 31 times out.

Finally, a loss of voltage comparator circuit 70 is provided to detect when the voltage Vm in the voltage storage 36 decays below a predetermined value. Specifically, the circuit receives the voltage Vm stored in the voltage storage circuit 36 at one input 71 and compares this value with a predetermined internally set reference voltage Vref received at its second input 73. Should the voltage Vm be less than the reference voltage as would occur if the transmitter is turned off or the stimulation pulses are not being received properly, an output signal on conductor 72 resets the error detection circuit 66, which disables the channel enable logic circuit 60. Once the channel enable logic circuit 60 has been disabled, four consecutive, identical programming data sequences must be received before the receiver can provide stimulation.

Summarizing, when the transmitter is turned on, the receiver logic will look for four consecutive, identical sequence of programming pulses. This part of the receiver operation defines a programming mode. Once these sequences are received, the error detection circuit 66 and the channel enable logic circuit 60 lock in and route the stimulation signal to the output switches to deliver the energy of the stimulation pulses to the electrodes after the bit counter circuit times out for each burst. This part of the receiver operation defines a stimulation mode. If the programming data fails to produce a desired physical response, the physician can reprogram the transmitter to form a new sequence of programming data, this sequence defining a different polarity or mono/biphasic capability, or a different combination of electrodes. Before reprogramming, the receiver must be disabled by turning off the transmitter or decoupling the antenna 20 such that the loss of voltage comparator circuit 70 resets the error detection circuit 66. When this occurs, the circuit can re-enter the programming mode. Alternatively, the receiver could monitor the programming signal continuously so that any change in programming would alter the contents of the receiver memory.

Figures 4, 5:
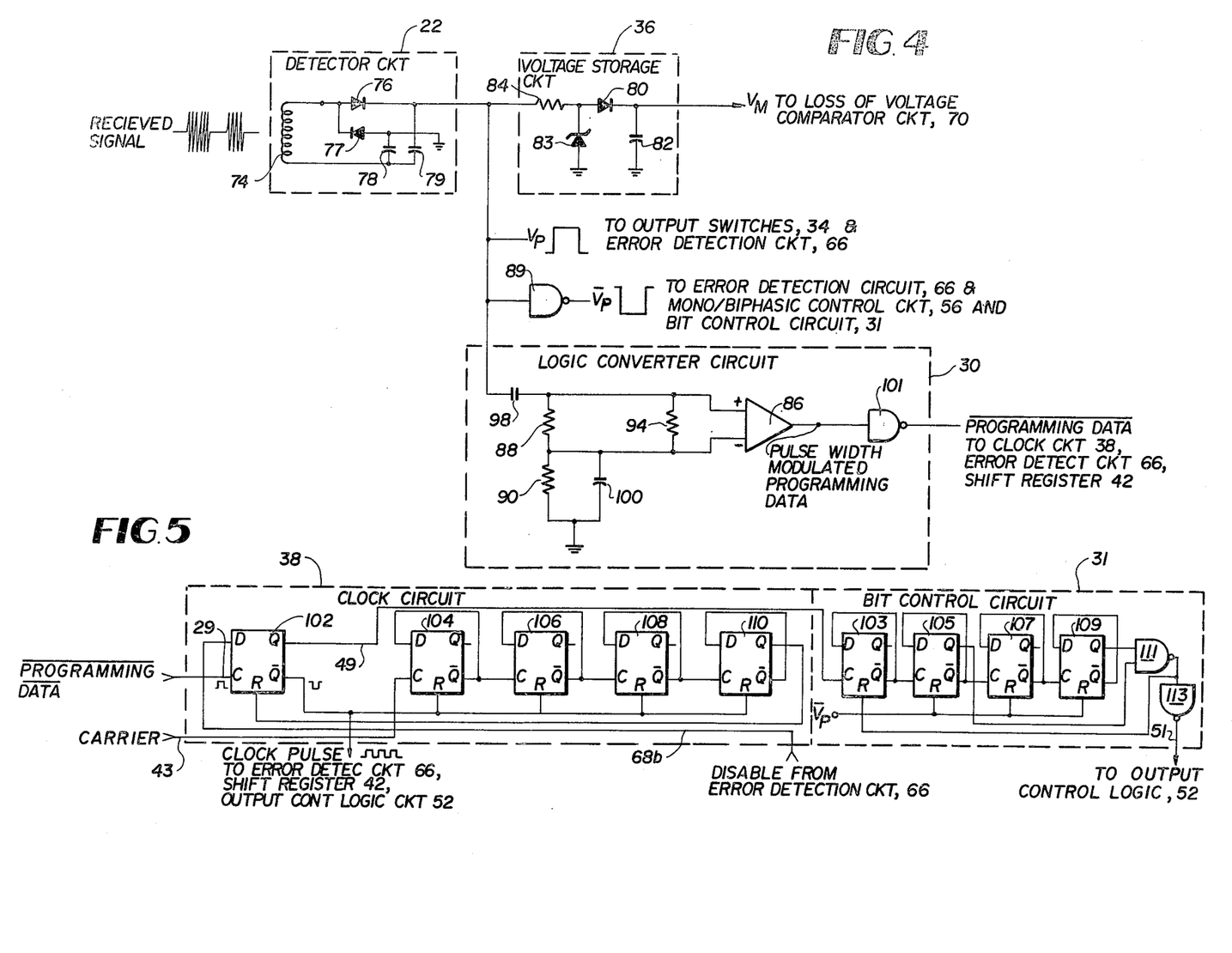
FIG. 4 shows a schematic diagram of the detector circuit, voltage storage circuit, and logic converter circuit of the receiver seen in FIG. 2.
FIG. 5 shows a schematic diagram of the clock circuit and the bit counter circuit of the receiver.

With reference to FIG. 4, the detector circuit 22, voltage storage circuit 36, and logic converter circuit 30, are shown in detail. More specifically, the transmitted stimulation pulses are inductively coupled transcutaneously to the receiver by inductor 74. Diode rectifiers 76 and 77 are connected to the inductor 74 to rectify the received signal. Capacitors 78 and 79 are chosen to respond only to envelope variations in the rectified signal so as to filter out the carrier signal 26 and provide a proper ground reference for the rectified signal.

The output of the detector circuit 22 is stored as voltage Vm in the voltage storage circuit 36 which comprises diode 80, capacitor 82, optional zener diode 83 and resistor 84. Alternatively, a rechargeable voltage source could be substituted for capacitor 82. The short-term output of the detector circuit 22 is the transmitted pulse $V_p$ which includes the pulse-width modulated programming data 28 on its envelope as seen in FIG. 3b. The transmitted pulse $V_p$ is applied to the logic converter circuit 30 which serves to decode the programming data 28 from the stimulation pulses $V_s$. The logic converter is well known in the art and comprises an operational amplifier 86, resistors 88, 90 and 94, and capacitors 98 and 100. Note that other configurations of the signal shaping passive components may also be used. The output of the logic converter 30 is inverted by the NAND gate 101 to form an inverted programming data signal which is applied to (a) the input 29 of the clock circuit 38 of FIG. 5; (b) the data input of the shift register 42 of FIG. 6; and (c) the input 65 of the error detection circuit 66 of FIG. 7. A NAND gate 89 is provided to form an inverted stimulation pulse $\overline{V}_p$.

The clock circuit 38 and bit counter circuit 31 are shown in detail in FIG. 5. The clock circuit consists of a control D-flip-flop 102 which includes a clock input 29, a data input, an inverted $\overline{Q}$ output, and a reset line. The rest of the clock circuit comprises four serially connected D flip-flops 104, 106, 108 and 110. These flip-flops are arranged as a divide by eight counter, with the clock input of the counter being derived from the carrier signal via conductor 43. The non-inverted Q output of the last flip-flop 110 of the counter is connected to the reset line of the control flip-flop 102. Also, the inverted $\overline{Q}$ output of the flip-flop 102 is connected to the reset lines of the counter flip-flops 104, 106, 108 and 110.

In operation, the pulse-width modulated programming data, which is inverted by NAND gate 101 of FIG. 4, is applied to the clock input 29 of the control flip-flop 102, so that the first falling edge in the signal will toggle the inverted $\overline{Q}$ output of this flip-flop to a logic low state. This signal resets the counter flip-flops 104, 106, 108 and 110 via their reset lines, such that the counter will start counting carrier pulses from zero. After eight cycles of the carrier-wave are counted, the non-inverted Q output of flip-flop 110 goes to logic high and resets the control flip-flop 102, terminating the pulse on its inverted $\overline{Q}$ output. The $\overline{Q}$ pulse from the control flip-flop 102 is the clock pulse 39 for the rest of the receiver circuit. It should be obvious to one skilled in the art that clock circuit 38 acts essentially as a monostable multivibrator, or one-shot circuit, with the pulse-width modulated data being used simply to trigger generation of the clock pulses at a frequency determined by the programming data and with a duty cycle determined by the carrier frequency.

The bit counter circuit 31 is also shown in FIG. 5. This circuit comprises D flip-flops 103, 105, 107, and 109 connected as a divide-by-ten counter, and NAND gates 111 and 113. The clock input to flip-flop 103 is provided by the non-inverted Q output of flip-flop 102 of the clock circuit 38. The inputs to NAND gate 111 are provided by the non-inverted Q outputs of flip-flops 105 and 109. Therefore, after ten bits of programming data have been received by the bit counter circuit 31, the output of NAND gate 111 goes logic low. This logic low signal is inverted by NAND gate 113 and applied to the output control logic circuit 52 via conductor 51 as will be described in detail below. The inverted transmitted pulse $\overline{V}_p$ is used to reset the counter via the reset inputs of of flip-flops 105, 107, and 109. Thus, the bit counter circuit is reset after each transmitted pulse.

Figure 6:
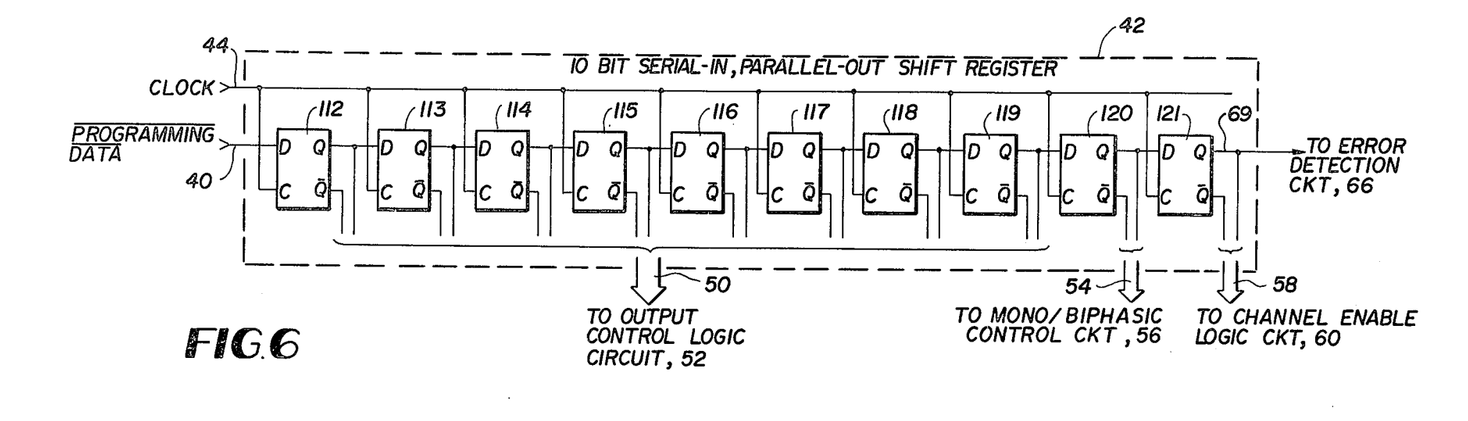
FIG. 6 shows a schematic diagram of the shift register of the receiver.

The shift register 42 of the receiver 12 is shown in FIG. 6, and comprises ten D-flip-flops 112-121 connected in a serial-in, parallel-out structure. In particular, the non-inverted Q output of the $n^{th}$ stage of the shift register 42 is connected to the data input of the succeeding or $n+1^{th}$ stage. The inverted programming data 28 is applied from NAND gate 101 of the logic converter circuit 30 in FIG. 4 to the data input of the first flip-flop 112 of the shift register 42 over conductor 40. The clock pulses 39 derived from the clock circuit 38 of FIG. 5 are applied to the clock inputs of each flip-flop 112-121 via conductor 44. The inverted $\overline{Q}$ and the non-inverted Q outputs of flip-flops 112-121 form the first output data bus 50 which connects a portion of the programming data 28 to the output control logic circuit 52 of FIG. 9. The non-inverted Q and inverted $\overline{Q}$ outputs of flip-flop 120 form the second output data bus 54 which connects a second portion of the programming data 28 to the mono/biphasic control circuit 56 of FIG. 8. Finally, the non-inverted Q and inverted $\overline{Q}$ outputs of flip-flop 121 form the third output data bus 58 for connecting the final bit of the shift register 42 to the channel enable logic circuit 60 of FIG. 8. Also, the non-inverted Q output 69 of the last flip-flop 121 is connected to the error detection circuit 66 of FIG. 7. The number of flip-flops in the shift register 42 is equal to the number of bits in the programming data sequence. Note that although ten bits are shown in the preferred embodiment, any number may be used such that other programmable parameters may be specified by the programming data. Also, it is envisioned that the shift register 42 comprises either volatile or non-volatile elements.

Figure 7:
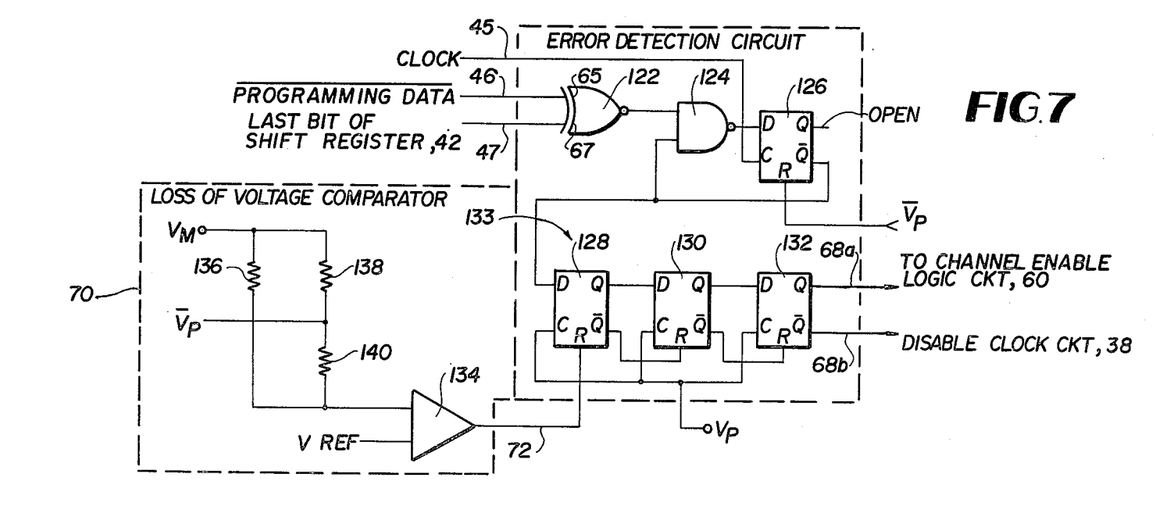
FIG. 7 shows a schematic diagram of the error detection circuit and the loss of voltage comparator circuit of the receiver.

The error detection circuit 66 is seen in FIG. 7 and comprises exclusive NOR (X-NOR) gate 122, NAND gate 124, and D flip-flops 126, 128, 130 and 132. The flip-flops 128, 130 and 132 define a three count ring counter 133. One of the inputs 65 of the X-NOR gate 122 is the inverted programming data 28 from NAND gate 101 of the logic converter in FIG. 4, while the other input 67 is provided by the non-inverted Q output 69 of the last flip-flop 121 of the shift register 42. The output of the X-NOR gate 122 is logic high if both of the inputs are high or both are low; otherwise, the output is low. Since the inputs to the X-NOR gate 122 are the input and output of the shift register 42, the output of the X-NOR gate 122 indicates whether the bits of the incoming programming data sequence match the bits of the previously-received programming data sequence. The output of the X-NOR gate 122 is connected as one input to the NAND gate 124, the output of which is connected to the data input of the flip-flop 126. The other input to the NAND gate 124 is provided by the inverted $\overline{Q}$ output of flip-flop 126. The clock pulses from clock circuit 38 of FIG. 5 are connected to the clock input of flip-flop 126. The inverted $\overline{Q}$ output of the flip-flop 126 is also connected to the data input of the ring counter 133. The non-inverted Q output of the last flip-flop 132 in the counter 133 is routed via conductor 68a to the channel enable logic circuit 60 of FIG. 7 and to the output control logic circuit 52 of FIG. 9 via conductor 68c. The inverted $\overline{Q}$ output of the flip-flop 132 is routed via conductor 68b to disable the clock circuit 38 by providing a logic low to the data input of the control flip-flop 102 in FIG. 5. Thus, a logic high on the inverted $\overline{Q}$ output of flip-flop 132 keeps the receiver in the programming mode and a logic low places the receiver in the stimulation mode. Finally, the reset line of flip-flop 126 is tied to the inverted transmitted pulse Vp provided by NAND gate 89 in FIG. 4, and the clock inputs of the flip-flops 128, 130 and 132 are tied to the non-inverted Vp signal.

FIG. 7 also shows the loss of voltage comparator circuit 70 which compares the energy Vm in the voltage storage circuit 36 of FIG. 4 to a predetermined voltage $V_{ref}$. In particular, the long-term voltage Vm is applied to one input of a comparator 134 via a resistor divider network 136, 138 and 140. The reference voltage, which is internally preset, is applied to the other input of the comparator 134. An output signal from the comparator 134 occurs whenever the voltage Vm is less than the predetermined reference voltage. As discussed above, this condition occurs when the receiver is no longer receiving stimulation pulses, or the pulses are not being received properly. The loss of voltage output is routed via conductor 72 to the reset line of the counter 133 in the error detection circuit. Thus, when a loss of voltage occurs, the error detection circuit is effectively reset and the receiver can re-enter the programming mode. Thereafter, four consecutive, identical programming data sequences must again be received before the receiver goes back into the stimulation mode.

The operation of the error detection circuit 66 of FIG. 7 will now be explained in detail. The inverted pulse $\overline{V}p$ resets flip-flop 126 for each transmitted burst received by the receiver. Therefore, the inverted $\overline{Q}$ output of flip-flop will be a logic high signal which is applied to NAND gate 124. As long as all the data bits of consecutively-received programming data sequences match, the output of X-NOR gate 122 will be logic high. Since both inputs of NAND gate 124 are logic high, its output is a logic low signal which is applied to the data input of flip-flop 126. Note that flip-flop 126 is clocked every bit of the programming data by the clock pulses 39 of FIG. 3d to keep the inverted $\overline{Q}$ output at logic high. If the inverted $\overline{Q}$ output of flip-flop 126 is logic high at the end of the stimulation pulse, this logic high signal is applied to the data input of the counter 133, indicating that consecutively-received programming data sequences are identical. After three identical sequences are consecutively-received and found to be identical with the initial sequence received, the ring counter 133 will provide a logic high output from the non-inverted Q output of flip-flop 132. This output is coupled via conductor 68a to the channel enable logic circuit 60 and indicates that the receiver may enter the stimulation mode. The inverted $\overline{Q}$ output of flip-flop 132 goes to logic low during the stimulation mode to disable the clock circuit 38 of FIG. 5 via the conductor 68b. It may also be used to disable the other parts of the receiver once the unit is programmed.

If any of the bits in the incoming programming data, however, do not match the bits in the previously-received programming data sequence, the output of X-NOR gate 122 is logic low and therefore the output of NAND gate 124 is logic high. This logic high signal causes the inverted $\overline{Q}$ output of flip-flop 126 to go to logic low, and thus NAND gate 124 will continue to provide a logic high output until the incoming data bits match the previously received data bits. In addition, a loss of voltage signal on conductor 72 may also be applied to reset the counter 133, such that the receiver can re-enter the programming mode after a loss of voltage.

Figure 8:
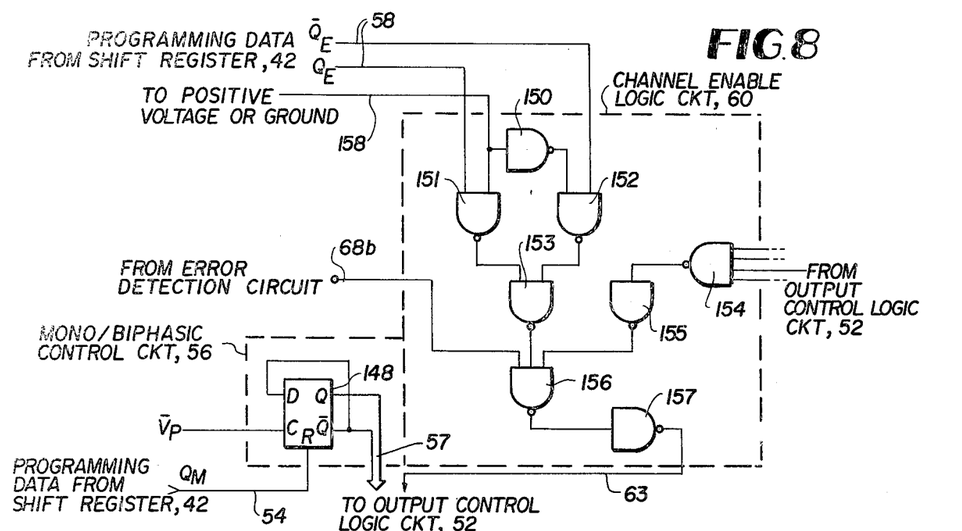
FIG. 8 shows a schematic diagram of the channel enable logic circuit and the mono/biphasic control circuit of the receiver.

Referring now to FIG. 8, the mono/biphasic control 56 and the channel enable logic 60 circuits are shown. More specifically, the mono/biphasic control circuit 56 comprises flip-flop 148. The mono/biphasic programming data Qm is applied to the reset line of flip-flop 148 via conductor 54 from flip-flop 120 of the shift register 42 in FIG. 6. The clock input of the flip-flop 148 is the inverted transmitted pulse $\overline{V}p$ which is provided by NAND gate 89 of FIG. 4. The data input of flip-flop 148 is connected to the inverted $\overline{Q}$ output of the flip-flop 148. The inverted $\overline{Q}$ and non-inverted Q outputs of flip-flop 148 are routed to the output control logic circuit of FIG. 9 via conductor bus 57.

As stated above, when monophasic operation occurs, the relative polarity of the stimulated electrodes remains constant throughout the stimulation mode. In the biphasic mode, however, this polarity alternates with each stimulation pulse. For example, if electrodes 18a and 18c are to be stimulated, and electrode 18a is to have positive polarity while electrode 18c a negative polarity; then during the biphasic mode, the polarity of these two electrodes will reverse with every stimulation pulse such that electrode 18a will be negative and electrode 18c will be positive.

In operation of the mono/biphasic control circuit 56, the inverted signal $\overline{V}p$ causes clocking at the end of the stimulation pulse since the flip-fop 148 is clocked with a rising edge. If the mono/biphasic bit Qm of the programming data 28 is logic low, which indicates monophasic mode, then the non-inverted Q output of flip-flop 148 will be logic high. The inverted $\overline{Q}$ output of flip-flop 148 will be logic low and this signal will be applied to the data input flip-flop 148. Since the flip-flop 148 is not reset every transmitted pulse, its outputs remain constant. However, should the mono/biphasic control bit be logic high, which indicates biphasic mode, then the inverted $\overline{Q}$ output of flip-flop 148 will be a logic high. This signal is applied to the data input of flip-flop 148. The non-inverted Q output of the flip-flop 148 will be a logic low. On each subsequent transmitted pulse, the flip-flop 148 will be reset since the bit Qm is logic high. Therefore, the outputs of the flip-flop 148 will alternate logic states. These outputs are routed via conductor bus 57 to the output control logic circuit of FIG. 9.

The channel enable logic circuit 60 is also shown in FIG. 8. This circuit comprises NAND gates 150-157. NAND gate 156 is the control gate and provides a logic low output only when the following conditions occur simultaneously: (a) the proper channel has been selected; (b) four consecutive, identical programming data sequences have been received by the error detection circuit 66 of FIG. 7; and (c) no invalid electrode combinations which would short the receiver have been selected. More specifically, the channel enable function is selected by NAND gates 150-153. In the preferred embodiment of the invention, it is desired that two redundant receivers will be present in the same receiver package. The use of two receivers provides greater flexibility in that the second receiver may be used for a different set of electrodes or as a backup should the initial receiver become defective.

In operation, each of the receivers includes a pin which will be grounded or tied to a positive voltage, depending on whether it will be designated channel A or B. This connection is applied via conductor 158 to the inputs of NAND gates 150 and 151. The other input of NAND gate 151 is the programming data bit $Q_E$ from the non-inverted Q output of flip-flop 121 of shift register 42 in FIG. 6. The signal on conductor 158 is inverted by NAND gate 150 and applied to one input of NAND gate 152. The other input of NAND gate 152 is the programming data bit $\overline{Q}_E$ from the inverted $\overline{Q}$ output of flip-flop 121 of shift register 42 in FIG. 6. Assuming that receiver A is to be utilized, conductor 158 will be tied to a positive voltage and the programming data bit $Q_E$ will be logic high. Therefore, the output of NAND gate 150 will be logic low and the output of NAND gate 152 will be logic high. However the output of NAND gate 151 will be logic low and therefore the output of NAND gate 153 will be logic high, indicating a channel has been selected. If receiver B is to be utilized, conductor 158 will be tied to ground and the programming data bit $\overline{Q}_E$ will be logic high. Therefore, the outputs of NAND gates 150 and 152 will be logic high and low, respectively. Since the output of NAND gate 152 is low, the output of NAND gate 153 is high and a channel has been selected. This output is applied to control NAND gate 156.

The output of the error detection circuit 66 of FIG. 7 is routed via conductor 68b to another input of NAND gate 156. This output will be logic high whenever four consecutive, identical programming data sequences have been received. The final input of control NAND gate 156 is from the output control logic circuit 52 of FIG. 9 via conductor 64. In particular, a low signal on this conductor indicates that an invalid electrode polarity combination has been selected for one of the electrodes by the physician. This low signal is applied to one input of NAND gate 154. The other three inputs of NAND gate 154 are derived from the output control logic of the other three electrodes. If an invalid combination is selected, the output of NAND gate 154 is logic high. This signal is inverted by NAND gate 155 to disable the control NAND gate 156. If no invalid combinations have been selected for each electrode, the output of NAND gate 155 is logic high. Therefore, since all the inputs of NAND gate 156 are logic high, its output is logic low. This signal is inverted by NAND gate 157 and applied via conductor 63 to the output control logic circuit 52 of FIG. 9. Therefore, a logic high signal on conductor 63 indicates that (a) the proper channel has been selected, (b) four consecutive and identical programming data sequences have been received, and (c) no invalid electrode combinations have been selected. This logic high signal indicates that the receiver is now in the stimulation mode.

Figure 9:
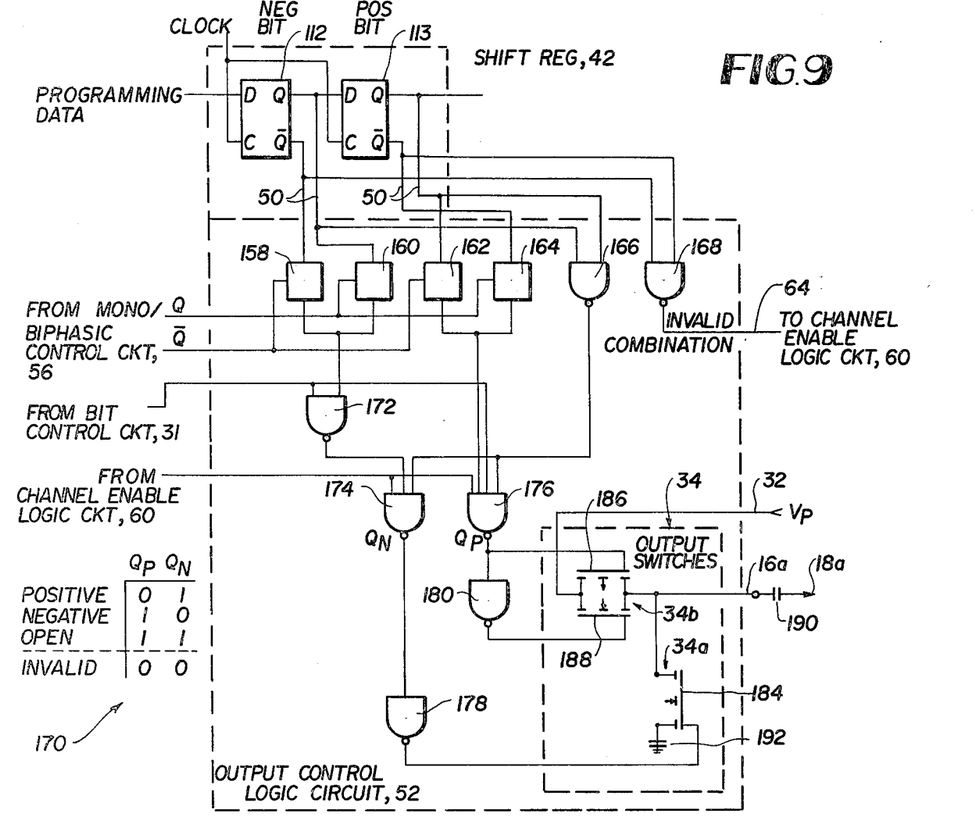
FIG. 9 shows a schematic diagram of the output control logic circuit and output switches of the receiver for one of the electrodes.

Turning now to FIG. 9, the output control logic 52 and the output switches 34 for one of the electrodes 18 is shown. It should be noted that the output control logic for the other three electrodes 18 will be identical to the circuit seen in FIG. 9, except they will have inputs from different flip-flops of the shift register 42 of FIG. 6. In operation, two programming data bits from each set of programming data 28 control each electrode 18. The use of two bits allows each electrode to assume a positive, negative or open circuit status with respect to the other electrodes. More specifically, if the negative polarity control bit Qn is stored in one of the flip-flops 112–121 of shift register 42 of FIG. 6, the positive polarity control bit Qp is stored in the next succeeding flip-flop. The flip-flops provide non-inverted and inverted outputs of the positive and negative polarity bits which are routed via conductor bus 50 to the output control logic circuit 52. The control bits may be put in any convenient order other than that described above.

Referring now specifically to FIG. 9, the output control logic for electrode 18a is provided. For this electrode, the negative and positive programming data bits are stored in flip-flops 112 and 113, respectively, of shift register 42. The negative and positive programming data bits for the other three electrodes are stored in flip-flops 114–121 of shift register 42 in FIG. 6. The inverted output $\overline{Q}n$ of flip-flop 112 is applied to a gated switch 158 and to one input of a NAND gate 168. The non-inverted output Qn of flip-flop 112 is applied to gated switch 160 and to one input of a NAND gate 166. The non-inverted output Qp of flip-flop 113 is applied to gated switch 162 and to the other input of NAND gate 168. The inverted output $\overline{Q}p$ of flip-flop 113 is applied to gated switch 164 and the second input of NAND gate 168. The output of NAND gate 166 will always be logic high unless the electrode is to be left open. The output of NAND gate 168 is applied via conductor 64 to the channel enable logic circuit 60 of FIG. 8 to indicate whether an invalid electrode combination has been selected. With reference to truth table 170, this condition occurs whenever both the non-inverted Q outputs of flip-flops 112 and 113 are logic low.

The gated switches 158, 160, 162 and 164 are controlled by the output of the mono/biphasic control circuit 56 of FIG. 8. In particular, the inverted $\overline{Q}$ output of flip-flop 148 of the mono/biphasic control circuit 56 is applied as the gate signal to gated switches 158 and 162. Also, the non-inverted Q output of flip-flop 148 is applied as the gate signal to gated switches 160 and 164. When the gate signal is logic high, the input to the gated switch is transmitted to the output of the gated switch.

The outputs of gated switches 158 and 160 are coupled to one input of NAND gate 172. The other input to NAND gate 172 is provided via conductor 51 by the bit counter circuit such that this gate is only turned on after ten data bits have been received. The output of NAND gate 172 is applied as one input to a negative control NAND gate 174. The other inputs to negative control NAND gate 174 are provided by the channel enable logic circuit 60 to FIG. 8 via conductor 63, and the output of NAND gate 166. The outputs of gated switches 162 and 164 are coupled to one input of a positive control NAND gate 176. The other inputs of this positive control NAND gate are provided by the channel logic circuit 60 via conductor 63, the output of NAND gate 166, and from the bit counter circuit 31 via conductor 51. The output of negative control NAND gate 174 is Qn in truth table 170 and is applied to output switch 34a and to NAND gate inverter 178. The output of positive control NAND gate 176 is Qp in truth table 170 and is applied to output switch 34b and to NAND gate inverter 180.

The output switch 34a comprises a n-channel MOS transistor 184 while output switch 34b comprises p-channel MOS transistor 186 and n-channel MOS transistor 188. The transmitted pulse $V_p$ can be applied to the electrode 18a via conductor 32 if the electrode has a programmed positive polarity. This pulse is coupled to electrode 18a by capacitor 190.

The operation of the output control logic 52 in FIG. 9 can be best explained by example. Assuming that electrode 18a is to have a positive polarity, then Qp is logic low and Qn is logic high as defined by truth table 170. Further, assume that monophasic capability is required such that the non-inverted Q output of flip-flop 148 in FIG. 8 is logic high and the inverted $\overline{Q}$ output is logic low. Recall that in the monophasic mode, these outputs will remain constant. Finally, it is assumed that (a) bit counter circuit 31 of FIG. 2 has determined that ten data bits have been received such that a logic high is present, on conductor 51, and (b) the channel enable logic circuit 60 of FIG. 8 has been enabled such that a logic high is present on conductor 63.

Under these conditions, the flip-flop 112 will have a logic high at its non-inverted Q output and a logic low at its inverted $\overline{Q}$ output. Further, the non-inverted Q output of flip-flop 113 will be logic low and the inverted $\overline{Q}$ output will be logic high. Since the monophasic mode is programmed, the non-inverted Q output of flip-flop 148 of FIG. 8 will gate a logic high through both gated switch 160 and gated switch 164. Gated switches 158 and 162 will not be enabled since the inverted $\overline{Q}$ output of the flip-flop 148 of FIG. 8 is logic low. Since the bit counter circuit 31 has provided a logic high output via conductor 51, the output of NAND gate 172 is a logic low signal which is applied to negative control NAND gate 174. The output of NAND gate 166 is logic high since electrode 18a is being programmed for receiving the stimulation pulse. Since the channel enable logic circuit of FIG. 8 has been enabled, all the inputs to positive control NAND gate 176 are logic high, and thus the output of this gate is logic low. Further, since a logic low is present at negative control NAND gate 174, the output of this gate is logic high.

The logic low signal from positive control NAND gate 176 is applied to the p-channel MOS transistor 186 of output switch 34b and to the NAND gate inverter 180. The output of the NAND gate is a logic high which turns the n-channel MOS transistor 188 of switch 34b ON. Similarly, the logic low signal turns ON p-channel MOS transistor 186. Since the output of the negative control NAND gate 174 is logic high, the output of NAND gate invertor 178 is logic low. This logic low signal holds n-channel MOS transistor 184 of which 34a OFF, thereby disconnecting the electrode from ground 192. Therefore, since transistors 186 and 188 of switch 34b are ON and transistor 184 of switch 34a OFF, the pulse $V_p$ is applied through output switch 34b and capacitor 190 to the electrode 18a.

Assume now that the physician requires the electrode 18a to have a negative or grounded polarity. In this case the output of negative control NAND gate 174 is logic low and the output of positive control NAND gate 176 is logic high. Therefore, n-channel MOS transistor 184 is ON, and the electrode 18a is pulled to ground potential 192. Note that the stimulation pulse cannot be transmitted through output switch 34b since both p-channel MOS transistor 186 and n-channel MOS transistor 188 are OFF.

It should be noted that if the channel enable logic circuit 60 is not enabled, as would occur if the proper channel has not been selected, four consecutive, identical data sequences haven't been received, or an invalid electrode has been selected, a logic low is present on conductor 63. This signal causes both Qn and Qp to be logic high and thus the electrode will be open. This open condition will also occur if a logic low is present on conductor 51, indicating that the bit counter 31 has not counted ten data bits.

Finally, should the physician require biphasic stimulation in the example above wherein electrode 18a is positive the outputs of the flip-flop 148 of FIG. 8 will alternate with each stimulation pulse. This alternation causes gated switches 158 and 162 to be enabled each time the outputs of flip-flop 148 in FIG. 8 alternate. The outputs of the switches 158 and 162 is a logic low signal which causes the outputs of the negative and positive control NAND gates 174 and 176 to alternate with each stimulation pulse. Therefore electrode 18a will go from positive polarity to ground and back again during three stimulation cycles. This cyling will continue as long as the mono/biphasic programming data bit is logic high.

The other electrodes 18b–18d can be programmed in a similar manner. Therefore, it can be seen that the receiver circuitry of the present invention provides a unique electronic system wherein the implanted electrodes can be independently programmed by the physician. In particular, each electrode is capable of dynamically assuming a positive, negative or open circuit status any time after implantation. This flexibility gives the physician an improved opportunity to attain a desired result with less inconvenience to the patient.

Although the preferred embodiment is shown to have four electrodes and ten data bits, it should be recognized that this should not be considered limiting. Any number of data bits and electrodes may be utilized.

The instant invention thus provides an efficient tissue stimulation system for controlling nervous or muscular disorders. In particular, the system can be used to stimulate the cervical area of the spinal cord, the brain, the cerebellum or the individual nerve fibers or bundles thereof to elicit motor, sensory, neurologic, physiologic or psychological responses. Alternatively, the system may be used to control muscle disorders, such as heart ailments. It is also envisioned that this system by utilized whenever stimulation is required for any other therapeutic reason.

It is anticipated that developments by the medical community will enable measurement of certain physiological parameters to determine the optimum stimulation parameters. The instant invention includes the concept of incorporating measurement circuitry into the implant for telemetry to assist in determining the best therapeutic regimen. The invention further includes incorporation of a microprocessor or logic circuitry into the implant to automatically reprogram stimulation parameters.

Although the invention has been described and illustrated in detail, it is clearly understood the same is by way of illustration and example only and is not to be taken by way of limitation. The spirit and scope of the present invention are to be limited only by the terms of the appended claims.

What is claimed:

1. An electronic tissue stimulator system, comprising:
   at least three electrodes to be implanted adjacent tissue to be stimulated in a patient;
   transmitting means for transmitting stimulation pulses to stimulate said electrodes and programming data to define which of said electrodes are to be stimulated and the electrical polarity of said electrodes relative to one another; and
   receiving means to be surgically implanted within said patient for receiving said stimulation pulses and said programming data, and for delivering said stimulation pulses to said electrodes in said electrical polarity as defined by said programming data.

2. An electronic tissue stimulator system as defined in claim 1 wherein said transmitting means includes means for generating a carrier wave in bursts to define said stimulation pulses, means for generating program data, and means for modulating said carrier wave with programming data.

3. An electronic tissue stimulator system as defined in claim 2 wherein said carrier wave means includes means for varying the parameters of said bursts to produce stimulation pulses having specific parameters.

4. An electronic tissue stimulator system as defined in claim 2 wherein said receiving means includes detector means to demodulate said stimulation pulses from said carrier wave.

5. An electronic tissue stimulator system as defined in claim 2 wherein said receiving means includes logic converter means for separating said programming data from said stimulation pulses.

6. An electronic tissue stimulator system as defined in claim 1 wherein said receiving means includes means for storing energy transmitted by said transmitting means.

7. An electronic tissue stimulator system as defined in claim 6 wherein said receiving means further includes memory means for storing said programming data.

8. An electronic tissue stimulator system as defined in claim 1 wherein said receiving means includes a mono/biphasic control means for controlling the polarity of said stimulated electrodes during application of consecutive stimulation pulses to said electrodes.

9. An electronic tissue stimulator system as defined in claim 8 wherein said mono/biphasic control means includes means responsive to said programming data to maintain the relative polarity of said stimulated electrodes constant during application of consecutive stimulation pulses, said operation defining a monophasic mode.

10. An electronic tissue stimulator system as defined in claim 8 wherein said mono/biphasic control means includes means responsive to said programming data to alternate the relative polarity of said stimulated electrodes during application of consecutive stimulation pulses, said operation defining a biphasic mode.

11. An electronic tissue stimulator system as defined in claim 1 wherein said transmitting means transmits programming data defining a pair of any two of said plurality of electrodes are to be stimulated and said receiving means delivers said stimulation pulses to said two defined electrodes.

12. An electronic tissue stimulator system as defined in claim 1 including output control logic connected to each of said electrodes and responsive to said programming data for delivering said stimulation pulses to said defined electrodes in said defined polarity.

13. A method of providing tissue stimulation, comprising:
   surgically-implanting a receiving means in a patient;
   surgically-implanting at least three electrodes connected to said receiving means adjacent tissue to be stimulated in said patient;
   selecting first programming data defining which of said electrodes will be stimulated and the electrical polarity of said electrodes relative to one another;
   transmitting said first selected programming data to said receiving means to produce a response;
   transmitting stimulation pulses to said receiving means to stimulate said electrodes in the electrical polarity defined by said previously transmitted first programming data with said stimulation pulses;
   selecting second programming data, different from said first programming data, defining a new combination of electrodes to be stimulated or a new polarity of said previously stimulated electrodes;
   transmitting said second selected programming data to said receiving means to produce a response; and
   transmitting stimulation pulses to said receiving means to stimulate said electrodes in the electrical polarity defined by said previously transmitted second programming data with said stimulation pulses.

14. A method of providing tissue stimulation as defined in claim 13 further including the step of selecting stimulation pulses to be transmitted to stimulate said electrodes at different frequencies.

15. A method of providing tissue stimulation as defined in claim 13 further including the step of selecting stimulation pulses to be transmitted to stimulate said electrodes with different amplitudes.

16. A method of providing tissue stimulation as defined in claim 13 further including the step of selecting said stimulation pulses to be transmitted to stimulate said electrodes with different pulse widths.

17. An electronic tissue stimulator system, comprising:
   a plurality of electrodes to be implanted adjacent tissue to be stimulated in a patient;
   transmitting means for transmitting stimulation pulses for stimulating said electrodes and programming data defining which of said electrodes are to be stimulated and the electrical polarity of said electrodes relative to one another;
   receiving means to be surgically implanted within said patient for receiving said stimulating pulses and said programming data, and for delivering the energy of said stimulation pulses to said electrodes and in said electrical polarity as defined by said programming data; and
   error detection means in said receiving means for comparing consecutive sequences of said programming data during a programming mode and controlling delivery of said stimulation pulses to said electrodes as a function of said comparison, said delivery of stimulation pulses defining a stimulation mode.

18. An electronic tissue stimulator system as defined in claim 17 wherein said error detection means determines a stimulation mode and permits delivery of stimulation pulses to said electrodes after a predetermined number of consecutive, identical sequences of said programming data are received by said receiving means.

19. An electronic tissue stimulator system as defined in claim 17 wherein said receiving means further includes a voltage storage means for storing the steady-state energy derived from said stimulation pulses.

20. An electronic tissue stimulator system as defined in claim 19 wherein said receiving means further includes a loss of voltage comparator means which continuously compares the energy in said voltage storage means with a predetermined voltage to control said error detection means.

21. An electronic tissue stimulator system as defined in claim 20 wherein said loss of voltage comparator means generates a reset signal when said energy in said voltage storage means is less than said predetermined voltage, and said error detection means includes means responsive to said reset for returning the system to a programming mode.

22. An electronic tissue stimulator system as defined in claim 17 wherein said receiving means further includes a channel enable means controlled by said programming data and said error detection means for preventing energization of said electrodes until said error detection means determines that a predetermined number of consecutive, identical sequences of said programming data have been received.

23. An electronic tissue stimulator system as defined in claim 22 wherein four consecutive, identical sequences of said programming data must be received to enable said error detection means.

24. An electronic tissue stimulator system as defined in claim 22 wherein said receiving means includes two redundant receivers controlled by said channel enable means, said channel enable means preventing energization of said electrodes until one of said receivers has been selected for operation.

25. An electronic tissue stimulator system as defined in claim 22 wherein said channel enable means further prevents energization of said electrodes if an invalid electrode programming combination is defined in said programming data.

26. An electronic tissue stimulator system as defined in claim 22 wherein said receiving means further includes a memory means for storing said programming data.

27. An electronic tissue stimulator system as defined in claim 26 wherein said memory means is a volatile memory means.

28. An electronic tissue stimulator system as defined in claim 26 wherein said memory means is a non-volatile memory means.

29. An electronic tissue stimulator system as defined in claim 28 wherein said receiving means includes an internal energy source.

30. An electronic tissue stimulator system as defined in claim 29 wherein said receiving means includes means for storing energy transmitted by said transmitting means.

31. An electronic tissue stimulator system as defined in claim 26 wherein said receiving means further includes a mono/biphasic control means connected to said memory means for controlling the relative polarity of said stimulated electrodes during application of consecutive stimulation pulses to said electrodes.

32. An electronic tissue stimulator system as defined in claim 31 wherein said receiving means further includes a voltage storage means for storing the steady-state energy derived from said stimulation pulses, said voltage storage means being connected to said memory means for retaining said programming data in said memory means between reception of said stimulation pulses.

33. An electronic tissue stimulator system as defined in claim 26 wherein said receiving means further includes an output control logic means connected to said memory means for controlling delivery of said stimulation pulses to said electrodes.

34. An electronic tissue stimulator system as defined in claim 33 wherein said channel enable means is connected to said output control logic, and
wherein said output control logic means is responsive to said channel enable means.

35. An electronic tissue stimulator system as defined in claim 33 including a plurality of output switches and
wherein said output logic means is connected to and controls said plurality of output switches as a function of said programming data to deliver said stimulation pulses to said electrodes.

36. An electronic tissue stimulator system as defined in claim 35 wherein said receiving means further includes delay means for controlling said output control logic means to delay the application of said stimulation pluses to said output switches.

37. An electronic tissue stimulator system as defined in claim 36 wherein said receiving means includes clock circuit means for controlling said delay means and for applying said programming data to said memory means, the period of said delay means being at least equal to the period of said programming data sequence such that said stimulation pulses are not applied to said output switches until after said programming data sequence has been stored in said memory means.

* * * * *